United States Patent [19]

Fujimoto et al.

[11] 4,282,245
[45] Aug. 4, 1981

[54] DIBENZOTHIEPIN DERIVATIVES AND A PROCESS FOR PRODUCING THE SAME

[75] Inventors: Yasuo Fujimoto, Tokyo; Shigeru Yamabe, Kobe, both of Japan

[73] Assignee: Nippon Chemiphar Co., Ltd., Tokyo, Japan

[21] Appl. No.: 41,560

[22] Filed: May 23, 1979

[30] Foreign Application Priority Data

Jun. 2, 1978 [JP] Japan .................................. 53-65691

[51] Int. Cl.$^3$ ..................... A61K 31/38; C07D 337/14
[52] U.S. Cl. .......................................... 424/275; 549/12
[58] Field of Search .......................... 549/12; 424/275

[56] References Cited
U.S. PATENT DOCUMENTS

| 4,000,288 | 12/1976 | Ackrell ................................. 549/12 |
| 4,101,667 | 7/1978 | Yamabe et al. ....................... 549/12 |
| 4,166,127 | 8/1979 | Yamabe et al. ....................... 549/12 |

FOREIGN PATENT DOCUMENTS

| 51-108081 | 9/1976 | Japan ................................. 549/12 |
| 51-108082 | 9/1976 | Japan ................................. 549/12 |

Primary Examiner—Alan Siegel
Attorney, Agent, or Firm—Oblon, Fisher, Spivak, McClelland & Maier

[57] ABSTRACT

A compound of the formula (I),

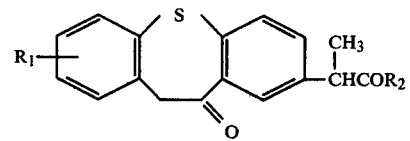

wherein $R_1$ represents a halogen atom, or a hydroxy, nitro, amino, trihalogenomethyl or lower alkoxy group having 1 to 5 carbon atoms, and $R_2$ represents a hydroxy or amino group is an antiinflammatory agent.

17 Claims, No Drawings

DIBENZOTHIEPIN DERIVATIVES AND A PROCESS FOR PRODUCING THE SAME

BACKGROUND OF THE INVENTION

This invention relates to novel dibenzothiepin derivatives represented by the following formula (I) and to a process for producing the same.

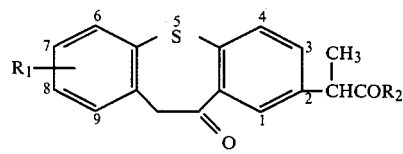

wherein $R_1$ represents a halogen atom, or a hydroxy, nitro, amino, trihalogenomethyl or lower alkoxy group having 1 to 5 carbon atoms, and $R_2$ represents a hydroxy or amino group.

The present inventors have studied a wide variety of compounds, and as a result of this study, they have found that dibenzothiepin derivatives of the formula (I) exhibit excellent antiinflammatory activities.

SUMMARY OF THE INVENTION

It is, therefore, one object of this invention to provide novel dibenzothiepin derivatives represented by the formula (I).

It is another object of this invention to provide dibenzothiepin derivatives of the formula (I) possessing a strong antiinflammatory action.

It is a further object of this invention to provide a novel process for producing the dibenzothiepin derivatives of the formula (I).

DETAILED DESCRIPTION OF THE PREFERRED EMBODIMENTS

The compounds of the formula (I) are divided into the following groups of the formulae (II) and (III),

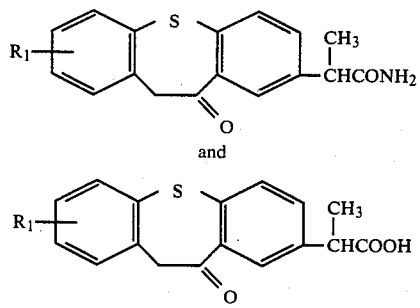

wherein $R_1$ is the same as defined above.

Of the compounds of the formula (I), particularly preferable are the compounds wherein $R_1$ represents a halogen atom or a lower alkoxy group having 1 to 5 carbon atoms.

In accordance with the present invention, the compounds of the formula (I) are produced by any one of the processes as shown below.

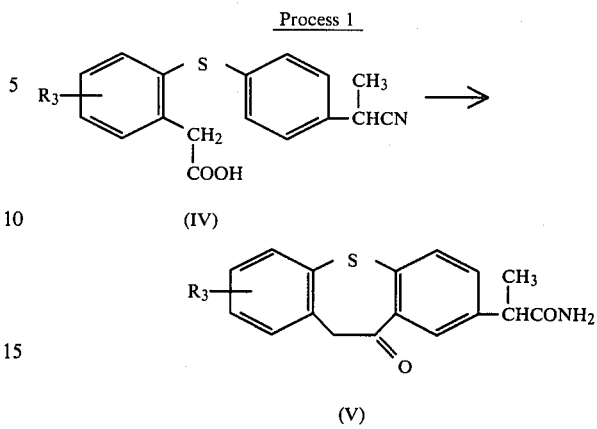

wherein $R_3$ represents a halogen atom, or a nitro, trihalogenomethyl or lower alkoxy group having 1 to 5 carbon atoms.

According to process 1, the compounds of the formula (V) are produced by cyclizing the compounds of the formula (IV) or active derivatives thereof.

The reaction is preferably conducted for 0.5 to 4 hours at 70° to 200° C. with or without a solvent such as benzene, toluene or xylene in the presence of a condensing agent. Suitable condensing agents to be used include, for example, polyphosphoric acid, polyphosphoric ester and the like.

The starting materials of the formula (IV) are produced according to the following scheme:

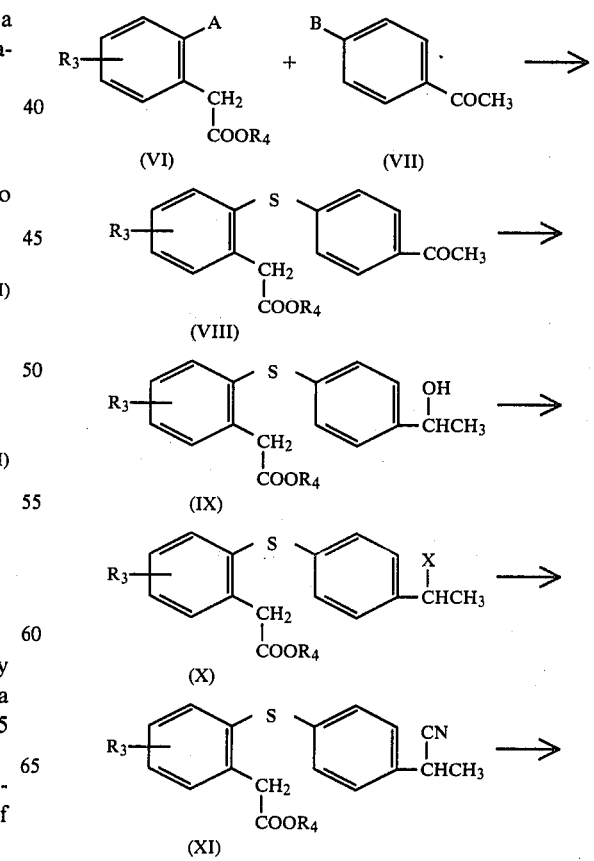

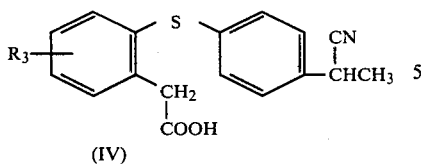

(IV)

wherein $R_3$ is the same as defined above, $R_4$ represents an ester residue, A and B represent a halogen atom, a mercapto group of a metallic salt thereof wherein A is a halogen atom when B is a mercapto group or a metallic salt thereof, and A is a mercapto group or a metallic salt thereof when B is a halogen atom, and X represents a halogen atom.

More specifically, the compounds of the formula (VI) are reacted with the acetophenone derivatives of the formula (VII) to produce the compounds of the formula (VIII), which are reduced to produce the compounds of the formula (IX), which are halogenated to produce the compounds of the formula (X), which are reacted with a metallic cyanide to produce the compounds of the formula (XI), which are hydrolyzed, whereby the compounds of the formula (IV) are obtained.

Process 2

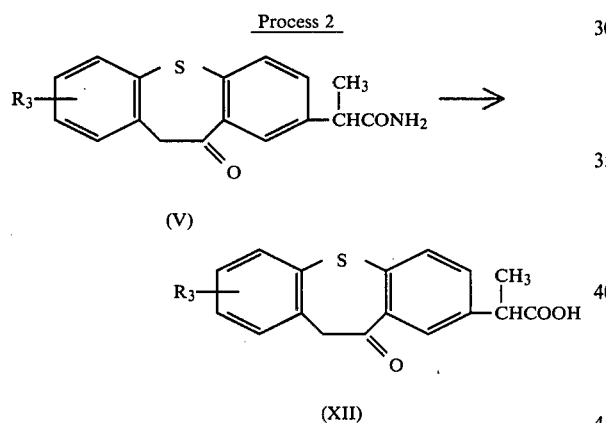

wherein $R_3$ is the same as defined above.

According to process 2, the compounds of the formula (XII) are produced by hydrolyzing the compounds of the formula (V).

The reaction is carried out by any conventional method, that is, in a solvent containing a small amount of water, for example, an alcohol such as methanol or ethanol in the presence of a catalyst such as potassium hydroxide, sodium hydroxide, hydrochloric acid or sulfuric acid at a temperature from room temperature to the boiling point of the solvent.

Process 3

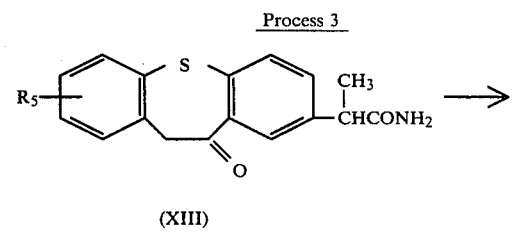

(XIII)

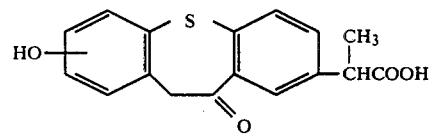

(XIV)

wherein $R_5$ represents a lower alkoxy group having 1 to 5 carbon atoms.

According to process 3, the compounds of the formula (XIV) are produced by hydrolyzing the compounds of the formula (XIII) in the presence of a catalyst such as hydrobromic acid.

The reaction is preferably conducted in an acid solvent such as acetic acid or formic acid at the boiling point of the solvent for 2 to 5 hours.

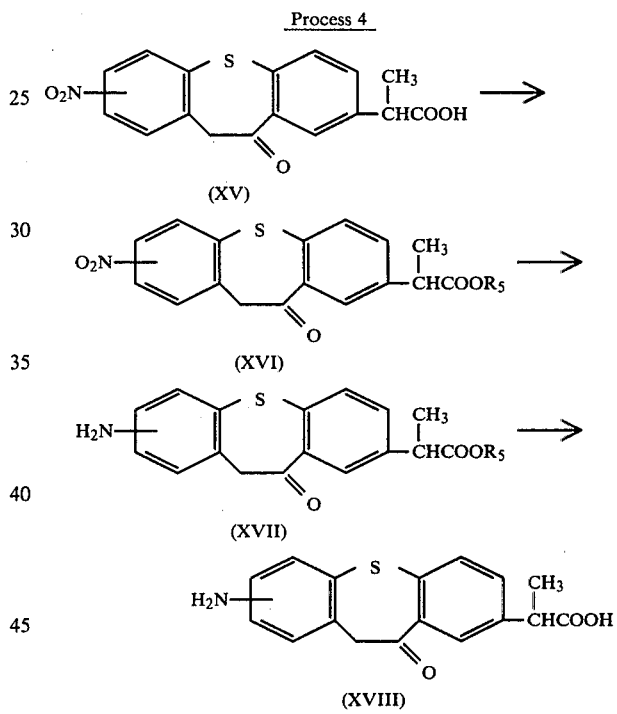

wherein $R_5$ represents a lower alkyl group having 1 to 5 carbon atoms.

According to process 4, the compounds of the formula (XVIII) are produced by reacting the compounds of the formula (XV) or reactive derivatives thereof with an alcohol having 1 to 5 carbon atoms or a reactive derivative thereof, reducing the resulting compounds of the formula (XVI), and then hydrolyzing the resulting compounds of the formula (XVII).

In producing the compounds of the formula (XVI) from the compounds of the formula (XV), the reaction may be conducted in an alcohol $R_5OH$, $R_5$ being the same as defined above, in the presence of a mineral acid such as sulfuric acid or hydrochloric acid at a temperature from room temperature to the boiling point of the solvent for 1 to 15 hours. The reactive derivatives of the alcohol include diazoalkane such as diazomethane. When the diazoalkane is used, the reaction is conducted in an ether solution containing the diazoalkane such as diazomethane at a temperature from 0° C. to room temperature.

In producing the compounds of the formula (XVII) from the compounds of the formula (XVI), the reaction is conducted by catalytic reduction using palladium carbon in a solvent such as acetone.

In producing the compounds of the formula (XVIII) from the compounds of the formula (XVII), the reaction is carried out by the conventional method; that is, the reaction is preferably conducted in water or a solvent containing some water, for example, an alcohol such as methanol or ethanol, in the presence of a catalyst such as potassium hydroxide or sodium hydroxide, at a temperature from room temperature to the boiling point of the solvent.

Process 5

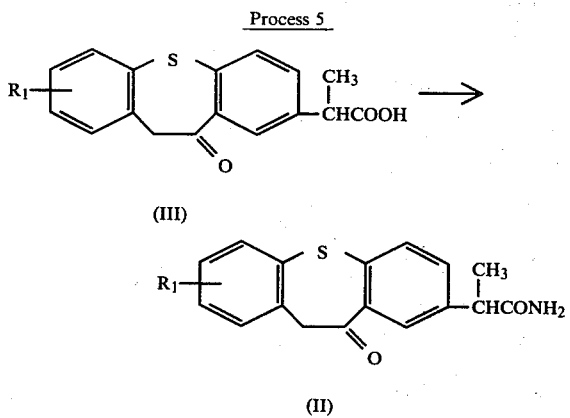

wherein $R_1$ is the same as defined above.

According to process 5, the compounds of the formula (II) are produced by reacting the compounds of the formula (III) or reactive derivatives thereof with ammonia. The reactive derivatives of the formula (III) include acid halides, mixtures of anhydrides and activated esters. The reaction may be conducted in an inert solvent such as chloroform, methylene chloride, benzene, toluene or tetrahydrofuran, which does not participate in the reaction, at a temperature from 0° C. to the boiling point of the solvent for 1 to 20 hours.

The compounds of the present invention represented by the formula (I) possess excellent antiinflammatory effects, as better understood by reference to the following experiments.

Male Wistar rats each weighing about 100 g, one group consisting of 5 to 7 animals, were orally given the compounds of the present invention and Indomethacin as a contrast, and edema was then induced in the hind paws by subcutaneous injection of 0.1 ml of 1% carrageenan one hour after the administration of the test compounds. Thereafter, the volumes of the hind paws with a predetermined lapse of time were measured by a volume differential meter. The results obtained are shown in Table 1.

| Test Compounds | Dosage (mg/kg) | Inhibition (%) (after 3 hours) | Rate to Indomethacin |
|---|---|---|---|
| Compound | | | |
| 1 | 2 | 67.8 | 5.2 |
| 2 | 2 | 48.2 | 1.9 |
| 3 | 2 | 40.4 | 1.2 |
| 4 | 2 | 46.8 | 1.4 |
| 5 | 2 | 61.6 | 2.7 |
| 6 | 2 | 58.4 | 2.29 |

-continued

| Test Compounds | Dosage (mg/kg) | Inhibition (%) (after 3 hours) | Rate to Indomethacin |
|---|---|---|---|
| 7 | 2 | 66.8 | 4.56 |
| 8 | 2 | 41.9 | 1.45 |
| Indomethacin | 2 | 34.5 | 1.00 |

Compound 1: 2-(10,11-dihydro-8-methoxy-11-oxodibenzo[b,f]thiepin-2-yl)-propionamide
Compound 2: 2-(10,11-dihydro-8-methoxy-11-oxodibenzo[b,f]thiepin-2-yl)-propionic acid
Compound 3: 2-(10,11-dihydro-8-ethoxy-11-oxodibenzo[b,f]thiepin-2-yl)-propionamide
Compound 4: 2-(8-chloro-10,11-dihydro-11-oxodibenzo[b,f]thiepin-2-yl)-propionamide
Compound 5: 2-(8-chloro-10,11-dihydro-11-oxodibenzo[b,f]thiepin-2-yl)-propionic acid
Compound 6: 2-(10,11-dihydro-8-fluoro-11-oxodibenzo[b,f]thiepin-2-yl)-propionamide
Compound 7: 2-(10,11-dihydro-8-fluoro-11-oxodibenzo[b,f]thiepin-2-yl)-propionic acid
Compound 8: 2-(10,11-dihydro-7-fluoro-11-oxodibenzo[b,f]thiepin-2-yl)-propionamide As can be seen from the results of Table 1, the present compounds have excellent effects in comparison with Indomethacin which has been widely used as an antiinflammatory drug.

The compounds of this invention exhibit both oral and parenteral activities and can be formulated in dosage forms for oral, parenteral, rectal or topical administration. Solid dosage forms for oral administration include capsules, tablets, pills, powders and granules. In the solid dosage forms, the active compounds are admixed with at least one inert diluent such as sucrose, lactose or starch. Such dosage forms can also comprise, as is the normal practice, additional substances other than the inert diluent, e.g., lubricating agents such as magnesium stearate. In the case of capsules, tablets and pills, the dosage forms may include buffering agents. Moreover, the tablets and pills can be prepared with an enteric coating.

Liquid dosage forms for oral administration include pharmaceutically acceptable emulsions, solutions, suspensions, syrups and elixirs containing inert diluents commonly used in the art such as purified water and alcohols. Besides the inert diluents, those compositions can also include adjuvants such as wetting agents, emulsifying and suspending agents, and sweetening, flavoring and perfuming agents. The preparations for parenteral administration according to this invention include sterile aqueous or non-aqueous solutions, suspensions and emulsions. Typical examples of the non-aqueous solvents or vehicles are propylene glycol, polyethylene glycol, vegetable oils such as olive oil, and injectable organic esters such as ethyl oleate.

Compositions for rectal administration are suppositories which may contain, in addition to the active substances, excipients such as cocoa butter or a suppository wax.

The dosage of the active ingredient in each of the compositions of this invention may be varied. However, it is necessary that the amount of the active ingredient be such that a suitable dosage form is obtained. Any selected dosage depends upon the desired therapeutic effect, the route of administration and the duration of treatment. Generally, suitable administration lies in a dosage of 0.3 to 20 mg/kg per human body weight per day for achieving effective relief of inflammation.

This invention is illustrated below in further detail with reference to several Examples, but the invention is not limited to these Examples.

EXAMPLE 1

2-(10,11-Dihydro-8-methoxy-11-oxodibenzo[b,f]thiepin-2-yl)-propionamide:

A mixture of 1.0 g of 2-[4-(α-cyanoethyl)phenylthio]-5-methoxy phenylacetic acid and 20.0 g of polyphosphoric acid was stirred at 75° C. for 3 hours. After the completion of the reaction, to the mixture was added ice water to decompose excess polyphosphoric acid, and the mixture was extracted with chloroform. The extract was washed in turn with water, a 5% sodium hydrogen carbonate solution and water and dried over anhydrous sodium sulfate. The solvent was removed by distillation to obtain a residue, which was chromatographed over silica gel and eluted with chloroform/methanol (100/1), thereby yielding a solid substance. This was recrystallized from ethanol to give 0.58 g (yield: 58%) of 2-(10,11-dihydro-8-methoxy-11-oxo dibenzo-[b,f]thiepin-2-yl)-propionamide as a powder having a melting point of 186°–188° C.

IR $\nu_{max}^{KBr}$ cm$^{-1}$: 3400 (NH), 3160 (NH), 1660 (C=O)

NMR (CDCl$_3$) δ: 1.40 (3H, d, J=7 Hz, C$\underline{H_3}$CH=), 3.76 (3H, s, C$\underline{H_3}$O), 4.24 (2H, s, ArC$\underline{H_2}$), 5.94 (2H, broad s, N$\underline{H_2}$), 6.56–7.56 (5H, m, aromatic protons), 8.02 (1H, d, 2 Hz, aromatic proton)

MS m/e: 327 (M+)

EXAMPLE 2

2-(10,11-Dihydro-8-methoxy-11-oxodibenzo[b,f]thiepin-2-yl)-propionic acid:

A mixture of 0.1 g of 2-(10,11-dihydro-8-methoxy-11-oxodibenzo[b,f]thiepin-2-yl)-propionamide, 1.0 g of sodium hydroxide, 10 ml of water and 20 ml of ethanol was refluxed for 3 hours. After the completion of the reaction, the solvent was removed by distillation to obtain a residue, to which was added ice water, and the mixture was acidified with hydrochloric acid and extracted with chloroform. The extract was washed with water and dried over anhydrous sodium sulfate. The solvent was distilled off to obtain a residue, which was chromatographed over silica gel and eluted with chloroform/benzene (4/1), thereby obtaining a solid substance. This substance was recrystallized from benzene-n-hexane to give 35 mg (yield: 35%) of 2-(10,11-dihydro-8-methoxy-11-oxodibenzo[b,f]thiepin-2-yl)-propionic acid as a powder having a melting point of 152°–153° C.

IR $\nu_{max}^{KBr}$ cm$^{-1}$: 1700, 1660 (C=O)

NMR (CDCl$_3$) δ: 1.46 (3H, d, J=7 Hz, C$\underline{H_3}$CH=), 3.70 (1H, q, J=7 Hz, CH$_3$C$\underline{H}$=), 3.76 (3H, s, C$\underline{H_3}$O), 4.28 (2H, s, ArC$\underline{H_2}$), 6.56–7.56 (5H, m, aromatic protons), 8.06 (1H, d, J=2 Hz, aromatic proton), 9.86 (1H, broad s, COO$\underline{H}$)

MS m/e: 328 (M+)

EXAMPLE 3

2-(10,11-Dihydro-8-ethoxy-11-oxodibenzo[b,f]thiepin-2-yl)-propionamide:

A mixture of 1.0 g of 2-[4-(α-cyanoethyl)phenylthio]-5-ethoxy phenylacetic acid and 20.0 g of polyphosphoric acid was stirred at 70°–75° C. for 3 hours. After the completion of the reaction, to this was added ice water to decompose excess polyphosphoric acid, and the mixture was extracted with chloroform. The extract was washed in turn with water, a 5% sodium hydrogen carbonate solution and water and dried over anhydrous sodium sulfate. The solvent was removed by distillation to obtain a residue, which was chromatographed over silica gel and eluted with chloroform/ethanol (100/1), whereby a solid substance was obtained. This substance was recrystallized from benzene-ether to give 0.3 g (yield: 30%) of 2-(10,11-dihydro-8-ethoxy-11-oxodibenzo[b,f]thiepin-2-yl)-propionamide as colorless granular crystals having a melting point of 128°–130° C.

IR $\nu_{max}^{KBr}$ cm$^{-1}$: 3400 (NH), 3200 (NH), 1660 (C=O)

NMR (CDCl$_3$)δ: 1.40 (3H, t, J=7 Hz, C$\underline{H_3}$CH$_2$—), 1.44 (3H, d, J=7 Hz, C$\underline{H_3}$CH=), 3.58 (1H, q, J=7 Hz, CH$_3$C$\underline{H}$=), 4.00 (2H, q, J=7 Hz, CH$_3$C$\underline{H_2}$—), 4.28 (2H, s, ArC$\underline{H_2}$), 5.80 (2H, broad s, CON$\underline{H_2}$), 6.60–7.60 (5H, m, aromatic protons), 8.04 (1H, s, aromatic proton).

MS m/e: 341 (M+).

EXAMPLE 4

2-(10,11-Dihydro-8-ethoxy-11-oxodibenzo[b,f]thiepin-2-yl)-propionic acid:

A mixture of 70 mg of 2-(10,11-dihydro-8-ethoxy-11-oxodibenzo[b,f]thiepin-2-yl)-propionamide, 800 mg of sodium hydroxide, 5 ml of water and 5 ml of ethanol was refluxed for 3 hours. After the completion of the reaction, the solvent was removed by distillation to obtain a residue, to which was added ice water, and the mixture was acidified with 10% hydrochloric acid and extracted with chloroform. The extract was washed with water and dried over anhydrous sodium sulfate. The solvent was distilled off to obtain a residue, which was chromatographed over silica gel and eluted with chloroform/benzene (4/1), thereby obtaining 26 mg (yield: 37%) of 2-(10,11-dihydro-8-ethoxy-11-oxodibenzo-[b,f]thiepin-2-yl)-propionic acid as an oil.

IR $\nu_{max}^{CHCl_3}$ cm$^{-1}$: 1710, 1670 (C=O)

NMR (CDCl$_3$)δ: 1.38 (3H, t, J=7 Hz, C$\underline{H_3}$CH$_2$), 1.48 (3H, d, J=7 Hz, C$\underline{H_3}$CH=), 3.72 (1H, q, J=7 Hz, CH$_3$C$\underline{H}$=), 4.00 (2H, s, ArC$\underline{H_2}$), 6.60–7.60 (5H, m, aromatic protons), 8.12 (1H, d, J=2 Hz, aromatic proton), 9.90 (1H, broad s, COO$\underline{H}$).

MS m/e: 342 (M+).

EXAMPLE 5

2-(8-Chloro-10,11-dihydro-11-oxodibenzo[b,f]thiepin-2-yl)-propionamide:

A mixture of 7.0 g of 2-[α-cyanoethyl)phenylthio]-5-chlorophenylacetic acid and 150.0 g of polyphosphoric acid was stirred at 105°–110° C. for 2 hours. After the completion of the reaction, to this was added ice water to decompose excess polyphosphoric acid, and the mixture was extracted with chloroform. The extract was washed in turn with water, a 5% sodium hydrogen carbonate solution and water and dried over anhydrous sodium sulfate. The solvent was removed by distillation to obtain a residue, which was crystallized from chloroform—n-hexane to give 6.1 g (yield: 87%) of 2-(chloro-10,11-dihydro-11-oxodibenzo[b,f]thiepin-2-yl)-propionamide as a powder having a melting point of 180°–181° C.

IR $\nu_{max}^{KBr}$ cm$^{-1}$: 3360 (NH), 3200 (NH), 1660 (C=O)

NMR (DMSO-d$_6$)δ: 1.35 (3H, d, J=7 Hz, C$\underline{H_3}$CH=), 3.70 (1H, q, J=7 Hz, CH$_3$C$\underline{H}$=), 4.36 (2H, s, ArC$\underline{H_2}$), 6.92 (2H, s, CON$\underline{H_2}$), 7.20–7.80 (5H, m, aromatic protons), 8.12 (1H, s, aromatic proton).

EXAMPLE 6

2-(8-Chloro-10,11-dihydro-11-oxodibenzo[b,f]thiepin-2-yl)-propionic acid:

A mixture of 0.4 g of 2-(8-chloro-10,11-dihydro-11-oxodibenzo[b,f]thiepin-2-yl)-propionamide, 6.0 g of sodium hydroxide, 50 ml of water and 60 ml of methanol was refluxed for 3 hours. The solvent was removed by distillation to obtain a residue, to which was added ice water, and the mixture was acidified with hydrochloric acid and extracted with chloroform. The extract was washed with water and dried over anhydrous sodium sulfate. The solvent was distilled off to obtain a residue, which was crystallized from benzene—n-hexane to give 190 mg (yield: 47%) of 2-(8-chloro-10,11-dihydro-11-oxodibenzo[b,f]thiepin-2-yl)-propionic acid as a powder having a melting point of 195°–196° C.

IR $\nu_{max}^{KBr}$ m$^{-1}$: 1680 (C=O)

NMR (DMSO-d$_6$)δ: 1.48 (3H, d, J=7 Hz, C$\underline{H}_3$CH=), 4.04 (1H, q, J=7 Hz, CH$_3$C$\underline{H}$=), 4.60 (2H, s, ArC$\underline{H}_2$), 7.70–8.24 (5H, m, aromatic protons), 8.48 (1H, s, aromatic proton).

EXAMPLE 7

2-(7-Chloro-10,11-dihydro-11-oxodibenzo[b,f]thiepin-2-yl)-propionamide:

A mixture of 0.5 g of 2-[4-α-cyanoethyl)phenylthio]-4-chlorophenylacetic acid and 10.0 g of polyphosphoric acid was stirred at 100° C. for 2 hours. After the completion of the reaction, to this was added ice water to decompose excess polyphosphoric acid, and the mixture was extracted with chloroform. The extract was washed in turn with water, a 5% sodium hydrogen carbonate solution and water and dried over anhydrous sodium sulfate. The solvent was removed by distillation to obtain a residue, which was crystallized form ethanol to give 370 mg (yield: 74%) of 2-(7-chloro-10,11-dihydro-11-oxodibenzo[b,f]thiepin-2-yl)-propionamide as yellowish brown plate crystals having a melting point of 207°–208° C.

IR $\nu_{max}^{KBr}$ cm$^{-1}$: 3400 (NH), 3200 (NH), 1640 (C=O)

NMR (DMSO-d$_6$)δ: 1.30 (3H, d, J=7 Hz, C$\underline{H}_3$CH=), 3.64 (1H, q, J=7 Hz, CH$_3$C$\underline{H}$=), 4.30 (2H, s, ArC$\underline{H}_2$), 6.80 (2H, broad s, CON$\underline{H}_2$), 7.32–7.76 (5H, m, aromatic protons), 8.00 (1H, s, aromatic proton).

EXAMPLE 8

2-(7-Chloro-10,11-dihydro-11-oxodibenzo[b,f]thiepin-2-yl)-propionic acid:

A mixture of 0.2 g of 2-(7-chloro-10,11-dihydro-11-oxodibenzo[b,f]thiepin-2-yl)-propionamide, 10 g of potassium hydroxide, 60 ml of water, 20 ml of tetrahydrofuran and 200 ml of methanol was refluxed for 5 hours. The solvent was removed by distillation to obtain a residue, to which was added ice water, and the mixture was acidified with hydrochloric acid and extracted with chloroform. The extract was washed with water and dried over anhydrous sodium sulfate. The solvent was distilled off to obtain a residue, which was chromatographed over silica gel and eluted with chloroform/benzene (3/1), thereby obtaining a solid substance. This was recrystallized from benzene—n-hexane to give 91 mg (yield: 45%) of 2-(7-chloro-10,11-dihydro-11-oxodibenzo[b,f]thiepin-2-yl)-propionic acid as light yellow granular crystals having a melting point of 142°–143° C.

IR $\nu_{max}^{KBr}$ CM$^{-1}$: 1700, 1680 (C=O)

NMR (CDCL$_3$)δ: 1.44 (3H, d, J=7 Hz, C$\underline{H}_3$CH=), 3.66 (1H, q, J=7 Hz, CH$_3$C$\underline{H}$=), 4.24 (2H, s, ArC$\underline{H}_2$), 7.10–7.56 (5H, m, aromatic protons), 8.02 (1H, d, J=2 Hz, aromatic proton), 9.50 (1H, broad s, COO$\underline{H}$).

EXAMPLE 9

2-(9-Chloro-10,11-dihydro-11-oxodibenzo[b,f]thiepin-2-yl)-propionamide:

A mixture of 700 mg of 2-chloro-6-[4-(1-cyanoethyl)-phenylthio]phenylacetic acid and 18 g of polyphosphoric acid was stirred at 70°–80° C. for 1.5 hours. After the completion of the reaction, to this was added ice water, and the mixture was extracted with chloroform. The extract was washed in turn with water, a 5% sodium hydrogen carbonate solution and water, and saturated a sodium chloride solution and dried over anhydrous sodium sulfate. The solvent was distilled off to obtain crystals, which were crystallized from ethanol to give 290 mg (yield: 42%) of 2-(9-chloro-10,11-dihydro-11-oxodibenzo[b,f]thiepin-2-yl)-propionamide as colorless crystals having a melting point of 195°–196° C.

IR $\nu_{max}^{CHCl_3}$ cm$^{-1}$: 3540, 3400 (CONH), 1680 (C=O)

NMR (DMSO-d$_6$)δ: 1.28 (3H, d, J=7 Hz, C$\underline{H}_3$CH=), 3.60 (1H, q, J=7 Hz, CH$_3$C$\underline{H}$=), 4.50 (2H, s, $\overline{CH_2}$CO), 6.80 (2H, s, CON$\underline{H}_2$), 7.10–7.60 (5H, m, aromatic protons), 8.00 (1H, d, C$_1\underline{H}$).

EXAMPLE 10

2-(9-Chloro-10,11-dihydro-11-oxodibenzo[b,f]thiepin-2-yl)propionic acid:

A mixture of 200 mg of 2-(9-chloro-10,11-dihydro-11-oxodibenzo[b,f]thiepin-2-yl)-propionamide, 3 g of sodium hydroxide, 25 ml of water, 30 ml of methanol and 2 ml of tetrahydrofuran was refluxed for 14 hours. After the completion of the reaction, the solvent was removed by distillation to obtain a residue, to which was added water, and the mixture was acidified with with 10% hydrochloric acid and then extracted with chloroform. The extract was washed with water and dried over anhydrous sodium sulfate. The solvent was distilled off to obtain crystals, which were chromatographed over silica gel and eluted with chloroform. The thus obtained product was recrystallized from ethyl acetate to give 95 mg (yield: 48%) of 2-(9-chloro-10,11-dihydro-11-oxodibenzo[b,f]thiepin-2-yl)-propionic acid as light yellow crystals having a melting point of 163°–164° C.

IR $\nu_{max}^{CHCl_3}$ cm$^{-1}$: 1710, 1680 (C=O)

NMR (DMSO-d$_6$)δ: 1.34 (3H, d, J=7 Hz, C$\underline{H}_3$CH=), 3.78 (1H, q, J=7 Hz, CH$_3$C$\underline{H}$=), 4.56 (2H, s, $\overline{CH_2}$CO), 7.20–7.80 (5H, m, aromatic protons), 8.00 (1H, $\overline{d}$, C$_1\underline{H}$).

EXAMPLE 11

2-(10,11-Dihydro-8-fluoro-11-oxodibenzo[b,f]thiepin-2-yl)-propionamide:

To 100 mg of 2-[4-(α-cyanoethyl)phenylthio]-5-fluorophenylacetic acid was added 2 g of polyphosphoric acid, and the mixture was stirred at 83° C. for 30 minutes. After the completion of the reaction, to this was added ice water, and the mixture was extracted with ethyl acetate. The extract was washed with a 1 N sodium hydroxide solution and a saturated sodium chloride solution and then dried over anhydrous sodium sulfate. The solvent was distilled off to obtain light yellow crystals, which were recrystallized from acetone—n-hexane to give 46 mg (yield: 46%) of 2-(10,11-dihydro-8-fluoro-11-oxodibenzo[b,f]thiepin-2-yl)-propionamide as light yellow crystals having a melting point of 224°–225° C.

IR $\nu_{max}^{KBr}$ cm$^{-1}$: 3380, 3200 (CONH$_2$), 1680, 1650 (C=O)

NMR (DMSO-d$_6$)δ: 1.28 (3H, d, J=7 Hz, C$\underline{H}_3$CH=), 3.62 (1H, q, J=7 Hz, CH$_3$C$\underline{H}$=), 4.33 (2H, s, C$\underline{H}_2$CO), 6.80 (1H, b.s, CON$\underline{H}_2$), 6.98–7.84 (6H, m, aromatic protons and CON$\underline{H}_2$), 8.01 (1H, d, J=2 Hz, C$_1\underline{H}$).

EXAMPLE 12

2-(10,11-Dihydro-8-fluoro-11-oxodibenzo[b,f]thiepin-2-yl)-propionic acid:

To a mixture of 150 mg of 2-(10,11-dihydro-8-fluoro-11-oxodibenzo[b,f]thiepin-2-yl)-propionamide and 1.5 ml of acetic acid was added 1.5 ml of hydrobromic acid, and the mixture was refluxed with stirring for 1 hour. To this was added ice water, and the resulting mixture was extracted with ethyl acetate. The extract was washed with a saturated sodium chloride solution and dried over anhydrous sodium sulfate. The solvent was distilled off to obtain brown crystals, which were chromatographed over 10 g of silica gel and eluted with chloroform/methanol (50/1). The thus obtained product was recrystallized from ethyl acetate—n-hexane to give 105 mg (yield: 70%) of 2-(10,11-dihydro-8-fluoro-11-oxodibenzo[b,f]-thiepin-2-yl)-propionic acid as light yellow crystals having a melting point of 213°–214° C.

IR $\nu_{max}^{KBr}$ cm$^{-1}$: 1700, 1680 (C=O)

NMR (acetone-d$_6$)δ: 1.41 (3H, d, J=7 Hz, C$\underline{H}_3$CH=), 3.75 (1H, q, J=7 Hz, CH$_3$C$\underline{H}$=), 4.31 (2H, s, C$\underline{H}_2$CO), 6.82–7.74 (5H, m, aromatic protons), 7.98 (1H, d, J=2 Hz, C$_1\underline{H}$).

EXAMPLE 13

2-(10,11-Dihydro-8-hydroxy-11-oxodibenzo[b,f]thiepin-2-yl)-propionic acid:

A mixture of 130 mg of 2-(10,11-dihydro-8-methoxy-11-oxodibenzo[b,f]thiepin-2-yl)-propionamide, 20 ml of hydrobromic acid and 8 ml of acetic acid was refluxed with stirring for 3 hours. The solvent was distilled off to obtain a residue, which was extracted with chloroform. The extract was washed with a saturated sodium chloride solution and dried over anhydrous sodium sulfate. The solvent was distilled off to obtain crude crystals, which were recrystallized from ethyl acetate—n-hexane to obtain 102 mg (yield: 82%) of 2-(10,11-dihydro-8-hydroxy-11-oxodibenzo[b,f]thiepin-2-yl)-propionic acid as a light yellow powder having a melting point of 216°–217° C.

IR $\nu_{max}^{CHCl_3}$ cm$^{-1}$: 1715, 1680 (C=O)

NMR (acetone-d$_6$)δ: 1.46 (3H, d, J=7 Hz, C$\underline{H}_3$CH=), 3.86 (1H, q, J=7 Hz, CH$_3$C$\underline{H}$=), 4.34 (2H, s, C$\underline{H}_2$CO), 6.70–8.28 (6H, m, aromatic protons).

EXAMPLE 14

2-(10,11-Dihydro-6-methoxy-11-oxodibenzo[b,f]thiepin-2-yl)-propionamide:

To 48 mg of 2-[4-(α-cyanoethyl)phenylthio]-3-methoxyphenylacetic acid was added 1 g of polyphosphoric acid, and the mixture was stirred at 70° C. for 1 hour. To this was added ice water, and the mixture was extracted with ethyl acetate. The extract was washed in turn with a 5% sodium hydroxide solution, water and a saturated sodium chloride solution and dried over anhydrous sodium sulfate. The solvent was removed by distillation to obtain a yellow oil, which was chromatographed over 3 g of silica gel and eluted with chloroform. The thus obtained product was recrystallized from chloroform-methanol to give 24 mg (yield: 50%) of 2-(10,11-dihydro-6-methoxy-11-oxodibenzo[b,f]thiepin-2-yl)-propionamide as a white powder having a melting point of 210°–211° C.

IR $\nu_{max}^{KBr}$ cm$^{-1}$: 3370, 3200 (NH$_2$), 1660 (C=O)

NMR ($_{DMSO-d_6}^{CDCl_3}$)δ: 1.44 (3H, d, J=7 Hz, C$\underline{H}_3$CH=), 3.70 (1H, q, J=7 Hz, CH$_3$C$\underline{H}$=), 3.86 (3H, s, OC$\underline{H}_3$), 4.31 (2H, s, C$\underline{H}_2$CO), 6.80–7.7 (6H, m, aromatic protons).

EXAMPLE 15

2-(10,11-Dihydro-6-methoxy-11-oxodibenzo[b,f]thiepin-2-yl)-proionic acid:

To a mixture of 273 mg of 2-(10,11-dihydro-6-methoxy-11-oxodibenzo[b,f]thiepin-2-yl)-propionamide and 8 ml of ethanol was added 800 mg of potassium hydroxide in 2 ml of water, and the resulting mixture was refluxed with stirring for 6 hours. The solvent or ethanol was distilled off to obtain a residue, to which was added water, and the mixture was washed with benzene. The aqueous layer was acidified with hydrochloric acid and extracted with ethyl acetate. The extract was washed with a saturated sodium chloride solution and dried over anhydrous sodium sulfate. The solvent was removed by distillation to obtain a yellowish-brown oil, which was chromatographed over 9 g silica gel and eluted with chloroform to obtain light yellow crystals. The crystals were recrystallized from benzene-n-hexane to obtain 165 mg (yield: 60%) of 2-(10,11-dihydro-6-methoxy-11-oxodibenzo-[b,f]thiepin-2-yl)-propionic acid as light yellow crystals having a melting point of 176°–178° C.

IR $\nu_{max}^{KBr}$ cm$^{-1}$: 1710, 1670 (C=O),

NMR (CDCl$_3$)δ: 1.50 (3H, d, J=7 Hz, =CHC$\underline{H}_3$), 3.80 (1H, q, J=7 Hz, =C$\underline{H}$CH$_3$), 3.86 (3H, s, OC$\underline{H}_3$), 4.33 (2H, s, —C$\underline{H}_2$CO—), 6.72–7.72 (6H, m, aromatic protons).

EXAMPLE 16

2-(10,11-Dihydro-7-fluoro-11-oxodibenzo[b,f]thiepin-2-yl)-propionamide:

To 1.2 g of 2-[4-(α-cyanoethyl)phenylthio]-4-fluorophenylacetic acid was added 25 g of polyphosphoric acid, and the mixture was stirred at 85° C. for 45 minutes. After cooling, to this was added ice water, and the mixture was extracted with ethyl acetate. The extract was washed with a saturated sodium hydrogen carbonate solution and a saturated sodium chloride solution and then dried over anhydrous sodium sulfate. The solvent was removed by distillation to obtain yellow crystals, which were recrystallized from benzene, thereby obtaining 0.6 g (yield: 50%) of 2-(10,11-dihydro-7-fluoro-11-oxodibenzo-[b,f]thiepin-2-yl)-propionamide as pale yellow crystals having a melting point of 176.5°–177.5° C.

IR $\nu_{max}^{KBr}$ cm$^{-1}$: 3400–3200 (NH$_2$), 1650 (C=O)

NMR($_{DMSO-d_6}^{CDCl_3}$)δ: 1.34 (3H, d, J=7 Hz, =CHCH$_3$), 3.60 (1H, q, J=7 Hz, =C$\underline{H}$CH$_3$), 4.22 (2H, s, —C$\underline{H}_2$CO—), 6.36 (1H, b.s, —CON$\underline{H}_2$), 6.90–8.00 (7H, m, aromatic protons and NH$_2$).

EXAMPLE 17

2-(10,11-Dihydro-7-fluoro-11-oxodibenzo[b,f]thiepin-2-yl)-propionic acid:

To a mixture of 300 mg of 2-(10,11-dihydro-7-fluoro-11-oxodibenzo[b,f]thiepin-2-yl)-propionamide and 3 ml of acetic acid was added 3 ml of hydrochloric acid, and the resulting mixture was stirred at 100° C. for 2 hours. After cooling, to this was added water, and the mixture was extracted with ethyl acetate. The extract was re-extracted with a dilute sodium hydroxide solution. The aqueous layer was acidified with hydrochloric acid and extracted with ethyl acetate. The extract was washed with a saturated sodium chloride solution and dried over anhydrous sodium sulfate. The solvent was removed by distillation to obtain yellow crystals, which were recrystallized from benzene, thereby obtaining 200 mg (yield: 67%) of 2-(10,11-dihydro-7-fluoro-11-oxodibenzo[b,f]thiepin-2-yl)-propionic acid as colorless crystals having a melting point of 147.5°–148° C.

IR $\nu_{max}^{KBr}$ cm$^{-1}$: 1690, 1670 (C=O)

NMR (CDCl$_3$)δ: 1.44 (3H, d, J=7 Hz, =CHC$\underline{H}_3$), 3.74 (1H, q, J=7 Hz, =C$\underline{H}$CH$_3$), 4.32 (2H, s, —C$\underline{H}_2$CO—), 7.30–8.14 (6H, m, aromatic protons).

EXAMPLE 18

2-(10,11-Dihydro-9-methoxy-11-oxodibenzo[b,f]thiepin-2-yl)-propionamide:

To 1.3 g of 2-[4-(α-cyanoethyl)phenylthio]-6-methoxyphenylacetic acid was added 15 g of polyphosphoric acid, and the mixture was stirred at 100° C. for 1 hour. After cooling, to this was added ice water, and the mixture was extracted with ethyl acetate. The extract was washed with a dilute sodium hydroxide solution and a saturated sodium chloride solution and then dried over anhydrous sodium sulfate. The solvent was distilled off to obtain a residue, which was chromatographed over 12 g of silica gel and eluted with chloroform to obtain light yellow crystals. The crystals were recrystallized from benzene to obtain 0.4 g (yield: 30%) of 2-(10,11-dihydro-9-methoxy-11-oxodibenzo[b,f]thiepin-2-yl)-propionamide as pale yellow crystals having a melting point of 178°–180° C.

IR $\nu_{max}^{KBr}$ cm$^{-1}$: 3400, 3200 (NH$_2$), 1655 (C=O)

NMR$_{(DMSO-d_6}$$^{CDCl_3})$δ: 1.38 (3H, d, J=7 Hz, =CHC$\underline{H}_3$), 3.54 (1H, q, J=7 Hz, =C$\underline{H}$CH$_3$), 3.79 (3H, s, —OC$\underline{H}_3$), 4.45 (2H, s, —C$\underline{H}_2$CO—), 5.87–6.25 (2H, b.s, —CON$\underline{H}_2$), 6.63–7.95 (6H, m, aromatic protons)

EXAMPLE 19

2-(10,11-Dihydro-9-methoxy-11-oxodibenzo[b,f]thiepin-2-yl)-propionic acid.

To a mixture of 180 mg of 2-(10,11-dihydro-9-methoxy-11-oxodibenzo[b,f]thiepin-2-yl)-propionamide and 5 ml of ethanol was added 700 mg of potassium hydroxide in 5 ml of water, and the resulting mixture was stirred at 75° C. for 1 hour and further at 85° C. for 2 hours. The solvent or ethanol was removed by distillation to obtain a mixture, to which was added water, and the resulting mixture washed with chloroform. The aqueous layer was acidified with hydrochloric acid and extracted with ethyl acetate. The extract was washed with a saturated sodium chloride solution and dried over anhydrous sodium sulfate. The solvent was distilled off to obtain a red oily substance, which was chromatographed over 3 g of silica gel and eluted with chloroform, thereby obtaining 48 mg (yield: 27%) of 2-(10,11-dihydro-9-methoxy-11-oxodibenzo[b,f]thiepin-2-yl)-propionic acid as a yellow oily substance.

IR $\nu_{max}^{KBr}$ cm$^{-1}$: 1710, 1680 (C=O)

NMR (CCl$_4$)δ: 1.42 (3H, d, J=7 Hz, =CHC$\underline{H}_3$), 3.68 (1H, q, J=7 Hz, =C$\underline{H}$CH$_3$), 3.84 (3H, s, —OCH$_3$), 4.36 (2H, s, —C$\underline{H}_2$CO—), 6.80–8.16 (6H, m, aromatic protons), 11.40 (1H, b.s, —COOH)

EXAMPLE 20

2-(10,11-Dihydro-7-methoxy-11-oxodibenzo[b,f]thiepin-2-yl)-propionamide:

To 1.90 g of 2-[4-(α-cyanoethyl)phenylthio]-4-methoxyphenylacetic acid was added 40 g of polyphosphoric acid, and the mixture was stirred at 80° C. for 1.5 hours. After cooling, to this was added ice water, and the mixture was extracted with ethyl acetate. The extract was washed with a 5% sodium hydroxide solution and a saturated sodium chloride solution and then dried over anhydrous sodium sulfate. The solvent was distilled off to obtain a yellow oil, which was chromatographed over 50 g of silica gel and eluted with chloroform-methanol (50:1) to obtain a light yellow oil. This was recrystallized from benzene to obtain 0.64 g (yield: 33%) of 2-(10,11-dihydro-7-methoxy-11-oxodibenzo[b,f]thiepin-2-yl)-propionamide as colorless crystals having a melting point of 154°–155° C.

IR $\nu_{max}^{KBr}$ cm$^{-1}$: 3390, 3200 (NH$_2$), 1650 (C=O).

NMR (CDCl$_3$)δ: 1.47 (3H, d, J=7 Hz, =CHC$\underline{H}_2$), 3.64 (1H, q, J=7 Hz, =C$\underline{H}$CH$_3$), 3.82 (3H, s, —OCH$_3$), 4.30 (2H, s, —C$\underline{H}_2$CO—), 5.76 (2H, b.s, —CONH$_2$), 6.89–8.10 (6H, m, aromatic protons)

EXAMPLE 21

2-(10,11-Dihydro-7-methoxy-11-oxodibenzo[b,f]thiepin-2-yl)-propionic acid:

To a mixture of 393 mg of 2-(10,11-dihydro-7-methoxy-11-oxodibenzo[b,f]thiepin-2-yl)-propionamide and 12 ml of ethanol was added 1.2 g of potassium hydroxide in 3 ml of water, and the mixture was refluxed with stirring for 7.5 hours. The solvent or ethanol was removed by distillation to obtain a mixture, to which was added water, and the resulting mixture was washed with benzene. The aqueous layer was acidified with hydrochloric acid and extracted with ethyl acetate. The extract was washed with a saturated sodium chloride solution and dried over anhydrous sodium sulfate. The solvent was distilled off to obtain an orange oil, which was chromatographed over 10 g of silica gel and eluted with chloroform, thereby obtaining 138 mg (yield: 33%) of 2-(10,11-dihydro-7-methoxy-11-oxodibenzo[b,f]thiepin-2-yl)-propionic acid as a light yellow oil.

IR $\nu_{max}^{CHCl_3}$ cm$^{-1}$: 1710, 1675 (C=O)

NMR (CDCl$_3$)δ: 1.40 (3H, d, J=7 Hz, =CHC$\underline{H}_3$), 3.68 (1H, q, J=7 Hz, =C$\underline{H}$CH$_3$), 3.71 (3H, s, —OC$\underline{H}_3$) 4.22 (2H, s, —C$\underline{H}_2$CO—) 6.80–8.15 (6H, m, aromatic protons)

EXAMPLE 22

2-(10,11-Dihydro-8-trifluoromethyl-11-oxodibenzo[b,f]thiepin-2-yl)-propionamide:

To 100 mg of 2-[4-(α-cyanoethyl)phenylthio]-5-trifluoromethyl phenylacetic acid was added 2 g of polyphosphoric acid, and the mixture was stirred at 85° C. for 45 minutes. After cooling, to this was added ice water, and the mixture was extracted with ethyl acetate. The extract was washed with a saturated sodium hydrogen carbonate solution and a saturated sodium chloride solution and thereafter dried over anhydrous sodium sulfate. The solvent was distilled off to obtain yellow crystals, which were recrystallized from benzene to obtain 40 mg (yield: 40%) of 2-(10,11-dihydro-8-trifluoromethyl-11-oxodibenzo[b,f]thiepin-2-yl)-propionamide as pale yellow crystals having a melting point of 159°–161° C.

IR $\nu_{max}^{KBr}$ cm$^{-1}$: 3380, 3200 (NH$_2$), 1670 (C=O)

NMR ($_{DMSO\text{-}d_6}{}^{CDCl_3}$)δ: 1.44 (3H, d, J=7 Hz, =CHC$\underline{H}_3$), 3.68 (1H, q, J=7 Hz, =C$\underline{H}$CH$_3$), 4.40 (2H, s, —C$\underline{H}_2$CO—), 6.10, 6.90 (2H, b.s, —CON$\underline{H}_2$), 7.54–8.16 (6H, m, aromatic protons)

EXAMPLE 23

2-(10,11-Dihydro-8-trifluoromethyl-11-oxodibenzo[b,f]thiepin-2-yl)-propionic acid:

To a mixture of 40 mg of 2-(10,11-dihydro-8-trifluoromethyl-11-oxodibenzo[b,f]thiepin-2-yl)-propionamide and 1 ml of ethanol was added 200 mg of sodium hydroxide in 1 ml of water, and the mixture was stirred at 75° C. for 5 hours. After cooling, the solvent or ethanol was removed by distillation to obtain a residue, to which was added water, and the resulting mixture was washed with chloroform. The aqueous layer was acidified with hydrochloric acid and extracted with ethyl acetate. The extract was washed with a saturated sodium chloride solution and dried over anhydrous sodium sulfate. The solvent was distilled off to obtain a yellow oil, which was thin-layer chromatographed and developed with chloroform-methanol (10:1), thereby obtaining 15 mg (yield: 38%) of 2-(10,11-dihydro-8-trifluoromethyl-11-oxodibenzo[b,f]thiepin-2-yl)-propionic acid as a light yellow oil.

IR $\nu_{max}^{CHCl_3}$ cm$^{-1}$: 1710, 1675 (C=O)

NMR (CDCl$_3$)δ: 1.49 (3H, d, J=7 Hz, =CHC$\underline{H}_3$), 3.72 (1H, q, J=7 Hz, =C$\underline{H}$CH$_3$), 4.41 (2H, s, —C$\underline{H}_2$CO—), 7.35–8.13 (6H, m, aromatic protons)

EXAMPLE 24

2-(10,11-Dihydro-8-nitro-11-oxodibenzo[b,f]thiepin-2-yl)-propionamide:

To 1.7 g of 2-[4-(α-cyanoethyl)-phenylthio]-5-nitrophenyl acetic acid was added 34 g of polyphosphoric acid, and the mixture was stirred at 90° C. for 2 hour. To this was added ice water, and the resulting mixture was extracted with ethyl acetate. The extract was washed with a 1% sodium hydroxide solution and a saturated sodium chloride solution and then dried over anhydrous sodium sulfate to obtain a residue. The solvent was removed by distillation to obtain a yellow oil, which was crystallized from methanol, and there was obtained 0.5 g (yield: 30%) of 2-(10,11-dihydro-8-nitro-11-oxodibenzo[b,f]thiepin-2-yl)-propionamide as a light yellow powder having a melting point of 207°–209° C.

IR $\nu_{max}^{KBr}$ cm$^{-1}$: 3380, 3190 (NH$_2$), 1670, 1650 (C=O)

NMR ($_{DMSO\text{-}d_6}{}^{CDCl_3}$)δ: 1.37 (3H, d, J=7 Hz, =CHC$\underline{H}_3$), 3.67 (1H, q, J=7 Hz, =C$\underline{H}$CH$_3$), 4.44 (2H, s, —C$\underline{H}_2$CO—), 6.50, 7.26 (2H, broad s, —CON$\underline{H}_2$), 7.53–8.27 (6H, m, aromatic protons)

EXAMPLE 25

2-(10,11-Dihydro-8-nitro-11-oxodibenzo[b,f]thiepin-2-yl)-propionic acid:

A mixture of 3 ml of conc. hydrochloric acid, 3 ml of acetic acid and 0.33 g of 2-(10,11-dihydro-8-nitro-11-oxodibenzo[b,f]thiepin-2-yl)-propionamide was refluxed with stirring for 3.5 hours. The reaction mixture was concentrated, and to this was added water. Threafter, the resulting mixture was extracted with ethyl acetate, and the extract was reextracted with a saturated sodium hydrogen carbonate solution. The extract was acidified with hydrochloric acid and extracted with ethyl acetate. The extract was washed with a saturated sodium chloride solution and dried over anhydrous sodium sulfate. The solvent was distilled off to obtain a brown solid substance, which was chromatographed over 6 g of silica gel and eluted with chloroform, and there were obtained light yellow crystals. The thus obtained crystals were recrystallized from chloroform to give 0.14 g (yield: 43%) of 2-(10,11-dihydro-8-nitro-11-oxodibenzo[b,f]thiepin-2-yl)-propionic acid as a light yellow powder having a melting point of 209.5°–211° C.

IR $\nu_{max}^{KBr}$ cm$^{-1}$: 1710, 1675 (C=O)

NMR (CDCl$_3$)δ: 1.47 (3H, d, J=7 Hz, =CHC$\underline{H}_3$), 3.70 (1H, q, J=7 Hz, =C$\underline{H}$CH$_3$), 4.42 (2H, s, —C$\underline{H}_2$CO—), 7.43–8.23 (6H, m, aromatic protons)

EXAMPLE 26

Methyl 2-(10,11-dihydro-8-nitro-11-oxodibenzo[b,f]-thiepin-2-yl)-propionate:

To 72 mg of 2-(10,11-dihydro-8-nitro-11-oxodibenzo[b,f]-thiepin-2-yl)-propionic acid were added 10 ml of a diazomethaneether solution and 1 ml of methanol, and the mixture was stirred at room temperature for 30 minutes. To this was added acetic acid, and the mixture was made alkaline with a saturated sodium hydrogen carbonate solution and then extracted with benzene. The extract was washed with a saturated sodium chloride solution and dried over anhydrous sodium sulfate. The solvent was removed by distillation to obtain a yellow oil, which was chromatographed over 2 g of silica gel and eluted with chloroform, thereby obtaining 44 mg (yield: 57%) of methyl 2-(10,11-dihydro-8-nitro-11-oxodibenzo[b,f]thiepin-2-yl)-propionate as a yellow oil.

IR $\nu_{max}^{CHCl_3}$ cm$^{-1}$: 1735, 1680 (C=O)

NMR (CDCl$_3$)δ: 1.50 (3H, d, J=7 Hz, =CHC$\underline{H}_3$), 3.65 (3H, s, —COOC$\underline{H}_3$), 3.75 (1H, q, J=7 Hz, =C$\underline{H}$CH$_3$), 4.45 (2H, s, —C$\underline{H}_2$CO—), 7.37–8.27 (6H, m, aromatic protons)

EXAMPLE 27

Methyl 2-(8-amino-10,11-dihydro-11-oxodibenzo[b,f]thiepin-2-yl)-propionate:

To a mixture of 40 mg of methyl 2-(10,11-dihydro-8-nitro-11-oxodibenzo[b,f]thiepin-2-yl)-propionate and 3 ml of acetone was added a small amount of 10% palladium carbon, and the resulting mixture was subjected to catalytic reduction. The reaction mixture was filtrated with a suction using cerite to remove the catalysts. The solvent was removed by distillation to obtain a yellow oil, which was chromatographed over 2 g of silica gel and eluted with chloroform, thereby obtaining 13 mg (yield: 36%) of methyl 2-(8-amino-10,11-dihydro-11-oxodibenzo[b,f]thiepin-2-yl)-propionate as a yellow oil.

IR $\nu_{max}^{CHCl_3}$ cm$^{-1}$: 3400 (NH$_2$), 1730, 1670 (C=O)

NMR (CDCl$_3$)δ: 1.46 (3H, d, J=7 Hz, =CHC$\underline{H}_3$), 3.58 (3H, s, —COOC$\underline{H}_3$), 3.70 (1H, q, J=7 Hz, =C$\underline{H}$CH$_3$), 4.22 (2H, s, —C$\underline{H}_2$CO—)

EXAMPLE 28

2-(8-Amino-10,11-dihydro-11-oxodibenzo[b,f]thiepin-2-yl)-propionic acid:

To a mixture of 78 mg of methyl 2-(8-amino-10,11-dihydro-11-oxodibenzo[b,f]thiepin-2-yl)-propionate and 3 ml of methanol was added with ice cooling 200 mg of potassium hydroxide in 3 ml of water, and the resulting mixture was stirred at room temperature for 6 hours.

After filtrating the reaction mixture to remove insoluble substances, the filtrate was acidified with hydrochloric acid and extracted with ethyl acetate. The extract was washed with a saturated sodium chloride solution and dried over anhydrous sodium sulfate. The solvent was removed by distillation to obtain a yellow solid substance, which was chromatographed over 2 g of silica gel and eluted with chloroform/methanol (50/1), and there were obtained yellow crystals. The thus obtained crystals were recrystallized from chloroform-methanol to obtain 49 mg (yield: 75%) of 2-(8-amino-10,11-dihydro-11-oxodibenzo[b,f]thiepin-2-yl)-propionic acid as light yellow crystals having a melting point of 189°–191° C.

IR $\nu_{max}^{KBr}$ cm$^{-1}$: 3360, 3280 (NH$_2$), 1710, 1650 (C=O)

NMR (acetone-d$_6$)δ: 1.43 (3H, d, J=7 Hz, =CHCH$_3$), 4.20 (2H, s, —CH$_2$CO—), 6.52 (1H, dd, J=9, 3 Hz, C$_7$H), 6.78 (1H, d, J=3 Hz, C$_9$H), 7.28–7.83 (3H, m, aromatic protons), 8.09 (1H, d, J=3 Hz, C$_1$H)

What is claimed is:

1. A compound of the formula (I),

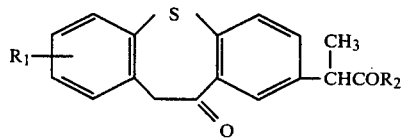

wherein R$_1$ represents a halogen atom, or a hydroxy, nitro, amino, trihalogenomethyl or lower alkoxy group having 1 to 5 carbon atoms, and R$_2$ represents a hydroxy or amino group.

2. A compound of the formula (II),

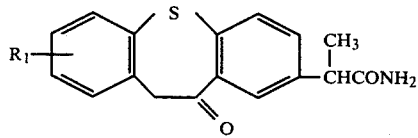

wherein R$_1$ represents a halogen arom, or a hydroxy, nitro, amino, trihalogenomethyl or lower alkoxy group having 1 to 5 carbon atoms.

3. A compound of the formula (III),

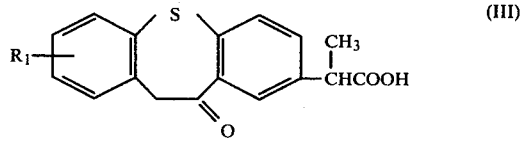

wherein R$_1$ represents a halogen atom, or a hydroxy, nitro, amino, trihalogenomethyl or lower alkoxy group having 1 to 5 carbon atoms.

4. 2-(10,11-Dihydro-8-fluoro-11-oxodibenzo[b,f]thiepin-2-yl)-propionamide.

5. 2-(10,11-Dihydro-8-methoxy-11-oxodibenzo[b,f]thiepin-2-yl)-propionic acid.

6. 2-(8-Chloro-10,11-dihydro-11-oxodibenzo[b,f]thiepin-2-yl)-propionic acid.

7. 2-(10,11-Dihydro-8-methoxy-11-oxodibenzo[b,f]thiepin-2-yl)-propionic acid.

8. 2-(10,11-Dihydro-7-fluoro-11-oxodibenzo[b,f]thiepin-2-yl)-propionic acid.

9. 2-(8-Chloro-10,11-dihydro-11-oxodibenzo[b,f]thiepin-2-yl)-propionamide.

10. 2-(10,11-Dihydro-8-ethoxy-11-oxodibenzo[b,f]thiepin-2-yl)-propionamide.

11. 2-(10,11-Dihydro-7-fluor-11-oxodibenzo[b,f]thiepin-2-yl)-propionamide.

12. 2-(10,11-Dihydro-8-methoxy-11-oxodibenzo[b,f]thiepin-2-yl)-propionamide.

13. 2-(10,11-Dihydro-8-fluoro-11-oxodibenzo[b,f]thiepin-2-yl)-propionic acid.

14. An antiinflammatory composition comprising an antiinflammatory effective amount of the compound according to claim 1 and an inert diluent.

15. An antiinflammatory composition comprising an antiinflammatory effective amount of the compound according to claim 2 and an inert diluent.

16. An antiinflammatory composition comprising an antiinflammatory effective amount of the compound according to claim 3 and an inert diluent.

17. An antiinflammatory composition comprising an antiinflammatory effective amount of the compound according to claim 4, 5, 6, 9, 10, 12 or 13 and an inert diluent.

* * * * *